United States Patent [19]

Widauer

[11] Patent Number: 4,590,191

[45] Date of Patent: May 20, 1986

[54] SOPORIFIC CONTAINING LORAZEPAM

[75] Inventor: Josef O. Widauer, Allschwil, Switzerland

[73] Assignee: Medichemie AG, Ettingen, Switzerland

[21] Appl. No.: 677,698

[22] Filed: Dec. 3, 1984

[30] Foreign Application Priority Data

Feb. 8, 1984 [DE] Fed. Rep. of Germany ....... 3404316

[51] Int. Cl.$^4$ .................... A61K 31/55; A61K 31/135
[52] U.S. Cl. .................................... 514/221; 514/648; 424/10
[58] Field of Search .................... 424/10, 244, 330; 514/221, 648

[56] References Cited

PUBLICATIONS

Chemical Abstracts 82: 51713k (1975).
Chemical Abstracts 87: 62717u (1977).

*Primary Examiner*—Jerome D. Goldberg
*Attorney, Agent, or Firm*—Yount & Tarolli

[57] ABSTRACT

A soporific containing lorazepam for oral or rectal administration, containing lorazepam and diphenhydramine or a diphenhydramine acid addition salt in the weight ratio of from 1:10 to 1:75.

The especially favorable weight ratio of lorazepam to diphenhydramine is 1:20 to 1:35.

The invention also relates to a process for the production of a soporific containing lorazepam and diphenhydramine.

1 Claim, No Drawings

SOPORIFIC CONTAINING LORAZEPAM

BACKGROUND OF THE INVENTION

This invention relates to a soporific, or sleep-inducing composition, containing lorazepam, for oral or rectal administration.

For many people, especially the ill, fulfilling the vital need for a recuperative sleep is ultimately possible only with medicinal aid. This has been for many decades a spur to the new and further development of still more suitable soporifics. Among these, the benzodiazepine hypnotics are broadly used. Representatives of this group with a long half-life result, after repeated use, in accumulation and morning hangover, while the use of benzodiazepines with a very short half-life leads to sedimentation effects and an increased dependence potential. In this group of hypnotics, lorazepam, with a medium half-life, is an important representative. Lorazepam is the unpatented (generic) name of 7-chlor-5-(2-chlorphenyl)-1,3-dihydro-3-hydroxy-2H-1,4 benzodiazepin-2-on. It is known, however, from many years of use of this substance, that its use as a hypnotic is not without problems, since with the giving of somewhat higher doses there are sometimes relatively strong side effects, such as muscle relaxation, ataxia and sedative after-effects, which may occur in the next few days. These side effects are often seen to be intensified, especially in older patients, even with single doses of 2 to 3 milligrams, so that individual doses of more than 1 mg lorazepam may be problematical as to the risk of side effects. Up to now it has not been possible to strengthen the effect of lorazepam without having to tolerate these side effects.

A need therefore exists for a soporific which is effective and, at the same time, well tolerated. According to experience, this goal cannot be well attained by increasing the dose of lorazepam.

SUMMARY OF THE INVENTION

The invention is directed toward the problem of providing the doctor with a soporific containing only relatively slight amounts of lorazepam, the use of which results in none of the side effects mentioned.

It has been found that the hypnotic effect of lorazepam can be decidedly intensified by combining it with diphenhydramine, without having to tolerate the additive toxicity to be expected from the sum of the toxicities of the components. Diphenhydramine is the generic name for 2-(diphenyl-methoxy)-N,N-dimethyl ethanamine; also known as (2-benzhydryloxy)-N,N-dimethylethylamine.

The subject of the invention is a soporific containing lorazepam, for oral or rectal administration, with the distinction that it contains (a) lorazepam and (b) diphenhydramine or an acid addition salt of diphenhydramine, in a weight ratio of from 1:10 to 1:75.

A weight ratio of from 1:20 to 1:35 has proven to be especially suitable.

Another subject of the invention is a process for the production of a sopoforic containing lorazepam, which is distinguished by the fact that lorazepam is mixed with diphenhydramine or an acid addition salt of diphenphydramine in a ratio, by weight, of from 1:10 to 1:75, and the composition obtained is processed into a form for oral or rectal administration.

This mixing takes place, preferably, in the weight ratio of from 1:20 to 1:35.

Suitable acids for the formation of the therapeutically useful acid addition salts of diphenhydramine are, in principle, any acids which form easily tolerated salts, such as for example, hydrochloric, phosphoric, salicylic, acetylsalicylic, tartaric, ascorbic, 4-sulfoamidobenzoic acid, etc. These are art recognized pharmaceutically acceptable salts. Generally, the diphenhydramine hydrochloride or the free base is used. But the other acid addition salts are generally just as suitable as the hydrochloride. According to which salt of diphenhydramine is chosen, the ideal mixing ratio between lorazepam and the diphenhydramine salt is varied according to the changed molecular weight of this salt.

As forms for oral administration for the combination of lorazepam and diphenhydramine there may be considered tablets, sugar-coated pills, capsules, powders and suspensions. Suitable forms for rectal administration are suppositories or enemas. Solid oral administration forms are generally preferred.

DETAILED DESCRIPTION

In oral administration to mice, the acute toxicity DL50 (lethal dose) for diphenhydramine hydrochloride is 312 mg/kg body weight, that of lorazepam 3178 mg/kg.

A combination of 25 parts by weight diphenhydramine hydrochloride and one part by weight lorazepam, calculated additively, therefore has a DL 50 of 323.2 mg/kg.

$$25 \frac{1}{312 \text{ mg/kg}} + 1 \frac{1}{3178} = \frac{26}{x} ; x = 323.2 \text{ mg/kg}$$

Diphenhydr.    Loraz.    DL 50 Comb.

Surprisingly, the toxicological testing in animal experiments of the combination of one part lorazepam and 25 parts by weight of diphenhydramine, as compared with the toxicological testing of diphenhydramine alone, showed a progressive relative decrease of acute toxicity, with increasing doses.

Thus, after oral administration to male mice, the DL 50 of the combination lies at 430 mg/kg. With further increases of the dose beyond the DL 50, the toxicity decreases as compared with that of pure diphenhydramine. Thus, for example, for diphenhydramine there is found a DL 95 of 645 mg/kg, but for the combination, this amounts to only 1622 mg/kg; that is, the combination is far more tolerable than diphenhydramine alone. From this finding it may be concluded that the combination is less toxic than the individual components.

This animal-experimental finding offers an additional safety factor for use of this new soporific in humans, in case high doses are taken with suicidal intention.

TABLE 1

Acute oral toxicity in white mice, of pure diphenhydramine HCl and of the combined preparation of 25 parts by weight diphenhydramine-HCl and 1 part by weight lorazepam.

| Lethality | Doses in mg/kg Body Weight | | | |
|---|---|---|---|---|
| | Diph. - HCl | | Combination | |
| DL 5 - 95 | Male | Female | Male | Female |
| 05 | 151 | 153 | 114 | 171 |
| 10 | 181 | 187 | 159 | 220 |
| 15 | 203 | 212 | 196 | 258 |
| 20 | 221 | 233 | 230 | 291 |
| 25 | 238 | 252 | 262 | 321 |

TABLE 1-continued

Acute oral toxicity in white mice, of pure diphenhydramine HCl and of the combined preparation of 25 parts by weight diphenhydramine-HCl and 1 part by weight lorazepam.

| Lethality DL 5 - 95 | Doses in mg/kg Body Weight | | | |
|---|---|---|---|---|
| | Diph. - HCl | | Combination | |
| | Male | Female | Male | Female |
| 30 | 253 | 269 | 293 | 349 |
| 35 | 268 | 286 | 325 | 378 |
| 40 | 282 | 303 | 358 | 406 |
| 45 | 297 | 320 | 392 | 436 |
| 50 | 312 | 338 | 430 | 466 |
| 55 | 328 | 356 | 470 | 500 |
| 60 | 345 | 376 | 516 | 536 |
| 65 | 363 | 398 | 568 | 576 |
| 70 | 384 | 424 | 630 | 623 |
| 75 | 409 | 453 | 705 | 679 |
| 80 | 439 | 489 | 803 | 749 |
| 85 | 478 | 537 | 940 | 843 |
| 90 | 536 | 608 | 1158 | 987 |
| 95 | 645 | 742 | 1622 | 1274 |

First clinical tests have shown that the combination of lorazepam and diphenhydramine has the desired increased effect, as compared with pure lorazepam, without having to obtain this at the cost of increased side effects. On the contrary, the number and intensity of side effects diminished instead.

The effect was tested of the combination of 1 mg lorazepam and 25 mg diphenhydramine hydrochloride in tablet form.

This soporific was given to medically informed patients of an old-age home, as well as to patients in general medical practice, in cases of clear difficulty in falling asleep and staying asleep, of various causes and intensity, and was tested for its effectiveness and toleration. The patient received, in each case, before going to bed, one tablet with some fluid. Patients or attendant personnel kept records on the most important parameters. The following data resulted:

TABLE 2

AGE DISTRIBUTION

| Age | Number of Patients |
|---|---|
| under 20 years | 8 |
| 20-29 years | 16 |
| 30-39 years | 25 |
| 40-49 years | 28 |
| 50-59 years | 22 |
| 60-69 years | 26 |
| 70-80 years | 31 |

TABLE 3

| Kind of Sleep Disturbance | Number of Patients | % of Total |
|---|---|---|
| Falling asleep | 42 | 27 |
| Staying asleep | 39 | 25 |
| Both | 75 | 48 |

TABLE 4

| Falling Asleep Time | Number of Patients | % of Total |
|---|---|---|
| Under 20 minutes | 12 | 7.7 |
| 20 minutes | 57 | 36.6 |
| 30 minutes | 51 | 32.7 |
| 40 minutes | 21 | 13.4 |
| 60 minutes | 9 | 5.8 |
| Over 60 minutes | 6 | 3.8 |

TABLE 5

| Duration of Sleep | Number of Patients | % of Total |
|---|---|---|
| Under 4 hours | 21 | 13.4 |
| 4-6 hours | 36 | 23 |
| 6-8 hours | 79 | 51 |
| Over 8 hours | 20 | 12.6 |

It was noted that 112 of 156 patients called the therapeutic effect good to very good. They slept evenly through the night, more than 6 hours as a rule, and felt fresh and restored in the morning. No side effects occurred.

The effect was judged adequate by 24 patients. They slept more than four hours.

The effect was called inadequate by 19 patients. Most of this group suffered from disturbances of a depressive nature.

The group of 92 patients who had already taken soporifics before described the new product, in a subjective comparison, as better, or at least as good.

The general toleration of the combination can be judged very good. Patients who complained of dizziness or sometimes headaches, had, as a rule, also complained of these difficulties earlier.

Based on experience up to now, this new combination has proven to be a soporific of good effectiveness and very well tolerated, with a wide spectrum of use. With the lower dosage of the individual components, it might have been expected that only the lighter, emotionally-caused falling-asleep disturbances would respond to the treatment. Remarkably, however, even staying-asleep disturbances and sleep disturbances in higher age groups, of various origins, are very favorably influenced, without the occurrence of serious side effects or paradoxical reactions. The comparison with sleep aids taken previously usually came out in favor of the experimental preparation.

The dosage of the two active substances is given from their activities.

Many years' experience with lorazepam as a hypnotic show that a single dose of 1 mg represents the amount received which has an especially good ratio between effect and tolerance. But the hypnotic or soporific effect of 1 mg lorazepam is often insufficient. Therefore, the dosage is often increased to 2 to 3 mg, with which, then, in individual cases, subjectively unpleasant side effects can occur.

Doses of 25 mg diphenhydramine (as a base or acid addition salt) have already shown, as compared with placebos, a highly significant hypnotic-sedative effect, which with an increase to the usual hypnotic dose of 50-75, no longer significantly increases. The small increase of effectiveness must then be purchased at the cost of noticeable side effects, such as dry mouth, urine retention and increased pressure on the eyes.

From this there is given a range, for the combination of from 1 to 3 parts by weight lorazepam and 25-75 parts by weight diphenhydramine or diphenhydramine acid addition salt.

Doses of 1 part by weight lorazepam and 20-35 parts by weight diphenhydramine or diphenhydramine acid addition salt have proved especially suitable and sufficient.

Single doses contain 1 to 3 mg lorazepam and about 25-100 mg diphenhydramine or a salt thereof.

Preferred single doses contain, generally, 1 mg lorazepam and 20–35 mg diphenhydramine or a salt thereof. Such doses have a decidedly low incidence of substance-specific side effects. They represent a minimum burden, therefore, as to tolerance. On the other hand, their effect is fully sufficient for most cases occurring in practice. As a rule, to the solid administration form there is added, besides the two active substances, also non-toxic pharmaceutical carrier substances, such as corn starch, wheat starch, talc, sodium bicarbonate, tartaric acid, citric acid, magnesium stearate, etc. The mixture of active substances and additives is pressed into tablets, as a rule. These can then be made into sugar-coated pills if necessary, especially if they are intended for pediatrics.

For the production of suppositories, the mixture of active substances is mixed with carrier substances and suppository material, melted in the suppository material and molded or pressed into suppositories.

Fluid administration forms are usually aqueous solutions of diphenhydramine salts, in which lorazepam is suspended. To stabilize the suspension, wetting agents or polyols are added, such as polyethylene glycol or polypropylene glycol, as well as glycol or glycerine ester.

EXAMPLE 1

Tablets. 2.5 kg diphenhydramine hydrochloride and 100 grams lorazepam are processed to a granulate with corn or potato starch, milk sugar, cellulose powder, magnesium stearate and talc, and pressed to form 100,000 tablets with a content of 1 mg lorazepam and 25 mg diphenphydramine hydrochloride each.

EXAMPLE 2

Sugar-coated pills. Tablets prepared according to Example 1 are covered with a sugar coating.

EXAMPLE 3

Tablets. Tablets prepared according to Example 1 are coated with a film which consists of polymers such as cellulose derivatives, polymethacrylic acid ester, polyvinyl pyrrolidone, or polyethylene glycol.

EXAMPLE 4

Tablets. 6.47 kilograms diphenhydramine salicylate are mixed with 100 grams lorazepam, as described in Example 1, granulated and then pressed into 200,000 tablets.

EXAMPLE 5

Capsules. 2.5 kilograms diphenhydramine hydrochloride and 0.1 kg lorazepam are mixed with the usual additives, as mentioned in Example 1, and poured, directly or after previous granulation, into 100,000 hard gelatine capsules with a content of 1 mg lorazepam and 25 mg diphenhydramine hydrochloride each.

EXAMPLE 6

Suppositories. 2.5 kilograms finely powdered diphenhydramine hydrochloride and 0.1 kg finely powdered lorazepam are mixed with suppository material, which consists mainly of hydrogenated vegetable fats, and molded into 100,000 suppositories with a content of 1 mg lorazepam and 25 mg diphenohydromine hydrochloride each.

What is claimed is:
1. A soporific consisting essentially of:
lorazepam,
diphenhydramine or a pharmaceutically acceptable acid addition salt thereof; and
an effective amount of non-pharmacologically active pharmaceutical carrier material,
wherein the ratio by weight of lorazepam to diphenhydramine or pharmaceutically acceptable acid addition salt thereof is 1:25.

* * * * *